US008136416B2

United States Patent
Uang et al.

(10) Patent No.: US 8,136,416 B2
(45) Date of Patent: Mar. 20, 2012

(54) PERSONAL NANOPARTICLE SAMPLER

(75) Inventors: Shi-Nian Uang, Taipei County (TW); Tung-Sheng Shih, Taipei County (TW); Chuen-Jinn Tsai, Hsinchu (TW); Cheng-Han Wu, Hsinchu (TW)

(73) Assignee: Institution of Occupational Safety and Health, Taipei (TW)

( * ) Notice: Subject to any disclaimer, the term of this patent is extended or adjusted under 35 U.S.C. 154(b) by 596 days.

(21) Appl. No.: 12/246,443

(22) Filed: Oct. 6, 2008

(65) Prior Publication Data

US 2009/0272202 A1 Nov. 5, 2009

(51) Int. Cl.
*G01N 1/10* (2006.01)
(52) U.S. Cl. .................................... 73/863.23
(58) Field of Classification Search ............. 73/863.23
See application file for complete search history.

(56) References Cited

U.S. PATENT DOCUMENTS

2004/0069047 A1* 4/2004 Coyle et al. ................. 73/28.04
2007/0269349 A1* 11/2007 Shih et al. .................... 422/101

* cited by examiner

*Primary Examiner* — Hezron E Williams
*Assistant Examiner* — Gregory J Redmann
(74) *Attorney, Agent, or Firm* — Browdy and Neimark, PLLC

(57) ABSTRACT

A personal nanoparticle sampler is disclosed to include a pre-classifier, a nozzle, a connector and a final filter pack. The connector and the final filter pack respectively accommodate a particle-sizing filter and a final filter to collect nanoparticles smaller than a diameter. The pre-classifier removes large particles to avoid clogging of the connector. The nozzle raises the airflow velocity to reduce the cut-off diameter of the particle-sizing filter without increasing the total flowrate, allowing the personal nanoparticle sampler to be used with a personal sampling pump.

11 Claims, 4 Drawing Sheets

PERSONAL NANOPARTICLE SAMPLER

BACKGROUND OF THE INVENTION

1. Field of the Invention

The present invention relates to air pollutant sampling equipments and more particularly, to a personal nanoparticle sampler for sampling workplace nanoparticles.

2. Description of the Related Art

In recent years, many researches and health-related studies show the impact of nanoparticle inhalation on human health. Further, nanoparticles of different compositions or particle sizes may have different impacts to human health.

In order to evaluate the impacts of nanoparticles to workers at the workplaces, it is necessary to collect nanoparticles smaller than a certain diameter, which is typically less than 100 nm, for laboratory analysis. Many nanoparticle sampling equipments are commercially available, including ELPI (Electrical Low-Pressure Impactor, Dekati Ltd. Model 3935), LPI (Low Pressure Impactor, Andersen model 20-930), MOUDI (Micro-Orifice Uniform Deposition Impactor, MSP model 100), and Nano-MOUDI (Nano Micro-orifice Uniform Deposition Impactor, MSP model 110). However, these equipments usually are large and heavy, and sample nanoparticles at a high flowrate and high pressure drop. They are not suitable to use with a personal pump. Therefore, they are merely used for fixed-location sampling. However, workers are usually moving among different areas having different particle concentrations. Sampling nanoparticles at fixed locations cannot reflect accurate exposure of workers to nanoparticles.

SUMMARY OF THE INVENTION

The present invention has been accomplished under the circumstances in view. It is the main objective of the present invention to provide a personal nanoparticle sampler, which collects nanoparticles smaller than a certain diameter which is typically less than 100 nm.

Another objective of the present invention is to provide a personal nanoparticle sampler, which has a low pressure drop and low flowrate, and can be used with a personal sampling pump carried by a worker to sample surrounding nanoparticles for further analysis.

To achieve these objectives of the present invention, the personal nanoparticle sampler comprises a pre-classifier, a nozzle, a connector, and a final filter pack. The pre-classifier comprises a first chamber and an air inlet. The air inlet extends from the first chamber to the outside of the pre-classifier. The nozzle is connected to the pre-classifier, comprising a passage disposed in communication with the first chamber of the pre-classifier. The passage has a cross section gradually reducing in direction apart from the first chamber. The connector is connected to one end of the nozzle opposite to the pre-classifier, comprising a second chamber disposed in communication with the passage of the nozzle. The final filter pack is connected to the connector, comprising a third chamber and a suction passage. The third chamber is disposed in communication with the second chamber of the connector. The suction passage extends from the third chamber to the outside of the final filter pack.

Further, the pre-classifier can be a cyclone separator. Further, the first chamber is comprised of a conical portion and a cylindrical portion. The connector further comprises a filter support mounted in the second chamber. The filter support has a plurality of perforations. The final filter pack comprises a top cover, a bottom cover, and a connector. The top cover and the bottom cover are fastened together, defining therein the third chamber. The connector defines therein the suction passage.

The personal nanoparticle sampler further comprises a rack. The rack comprises a top plate, two sliding rods, a bottom plate, and two springs. The top plate is stopped outside the final filter pack. The sliding rods are connected in parallel to the top plate. The bottom plate is coupled to the periphery of the pre-classifier and movable along the sliding rods. The springs are bilaterally connected between the top plate and the bottom plate.

The personal nanoparticle sampler further comprises a particle-sizing filter mounted in the second chamber of the connector, and a final filter mounted in the third chamber of the final filter pack. Further, the particle-sizing filter can be a polycarbonate track etch membrane.

Further, the passage of the nozzle has a circular cross section, and an outlet disposed at one end thereof remote from the first chamber. The outlet has a diameter smaller than 1.5 mm, preferably within 0.6 mm~1 mm. Further, the outlet has an airflow velocity of 85 m/sec~165 m/sec, preferably within 110 m/sec~115 m/sec.

DETAILED DESCRIPTION OF THE INVENTION

Figure 1:
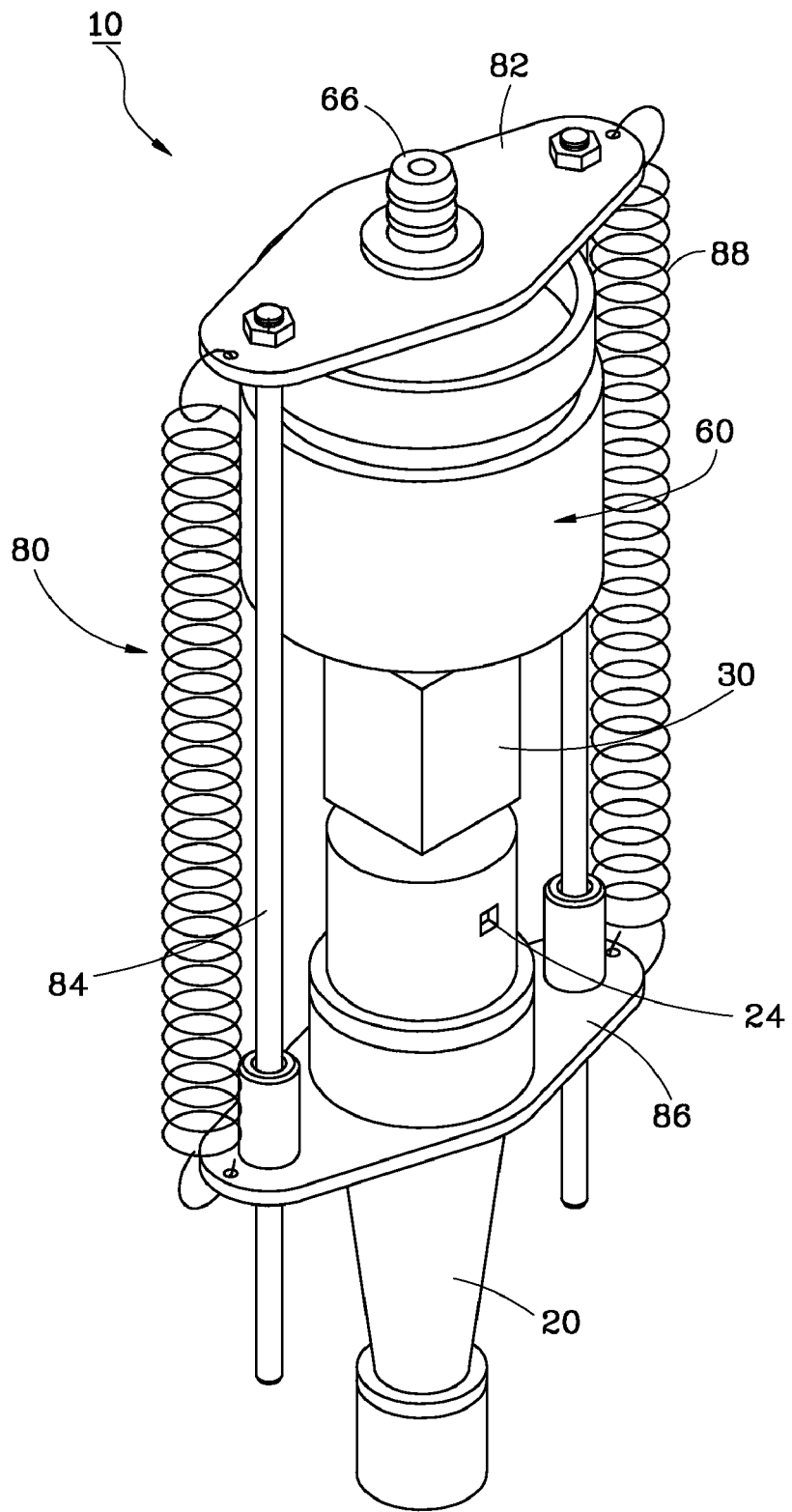
FIG. 1 is the perspective view of the assembly of the personal nanoparticle sampler in accordance with the present invention.
Figure 2:
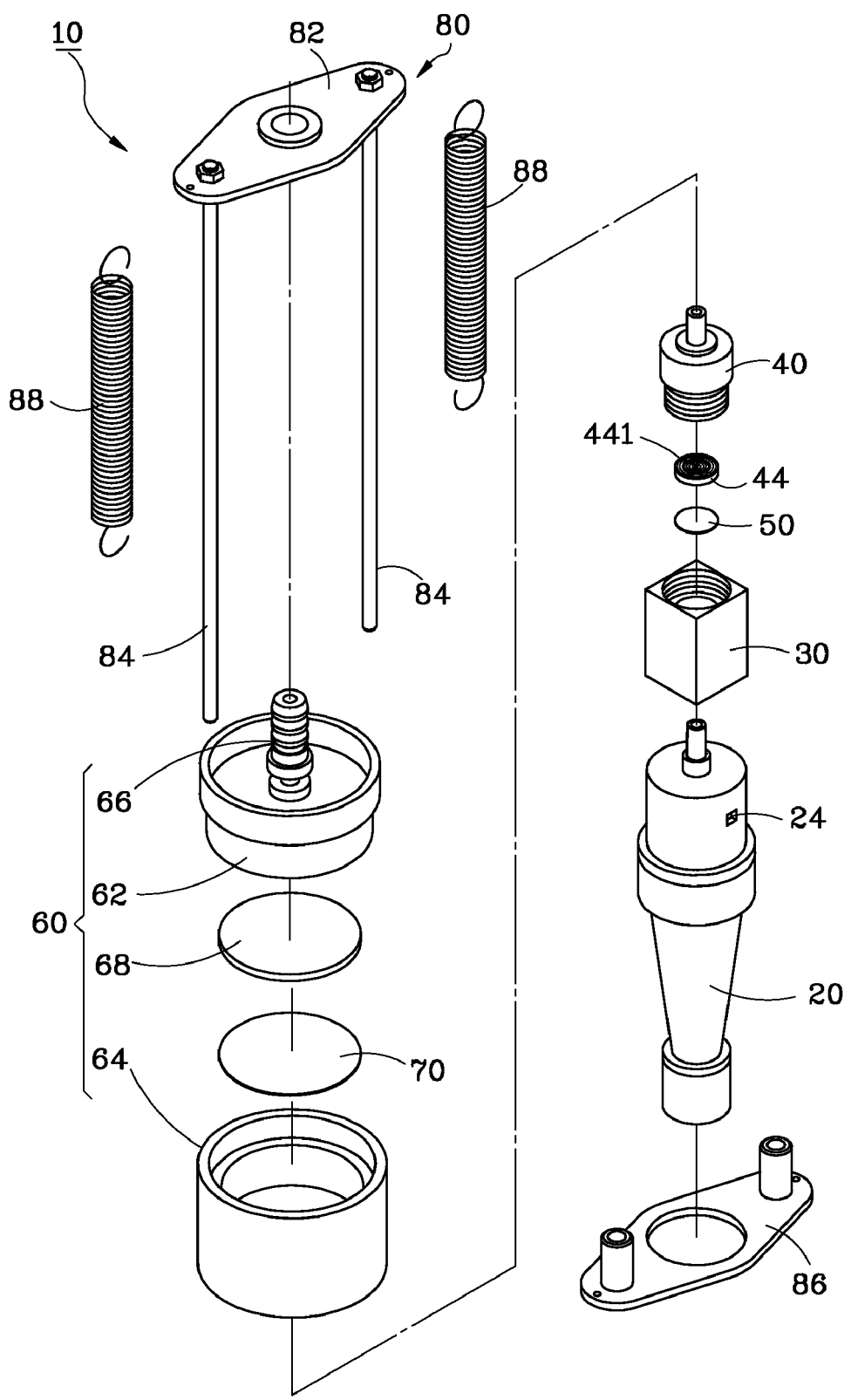
FIG. 2 is an exploded view of the personal nanoparticle sampler in accordance with the present invention.
Figure 3:
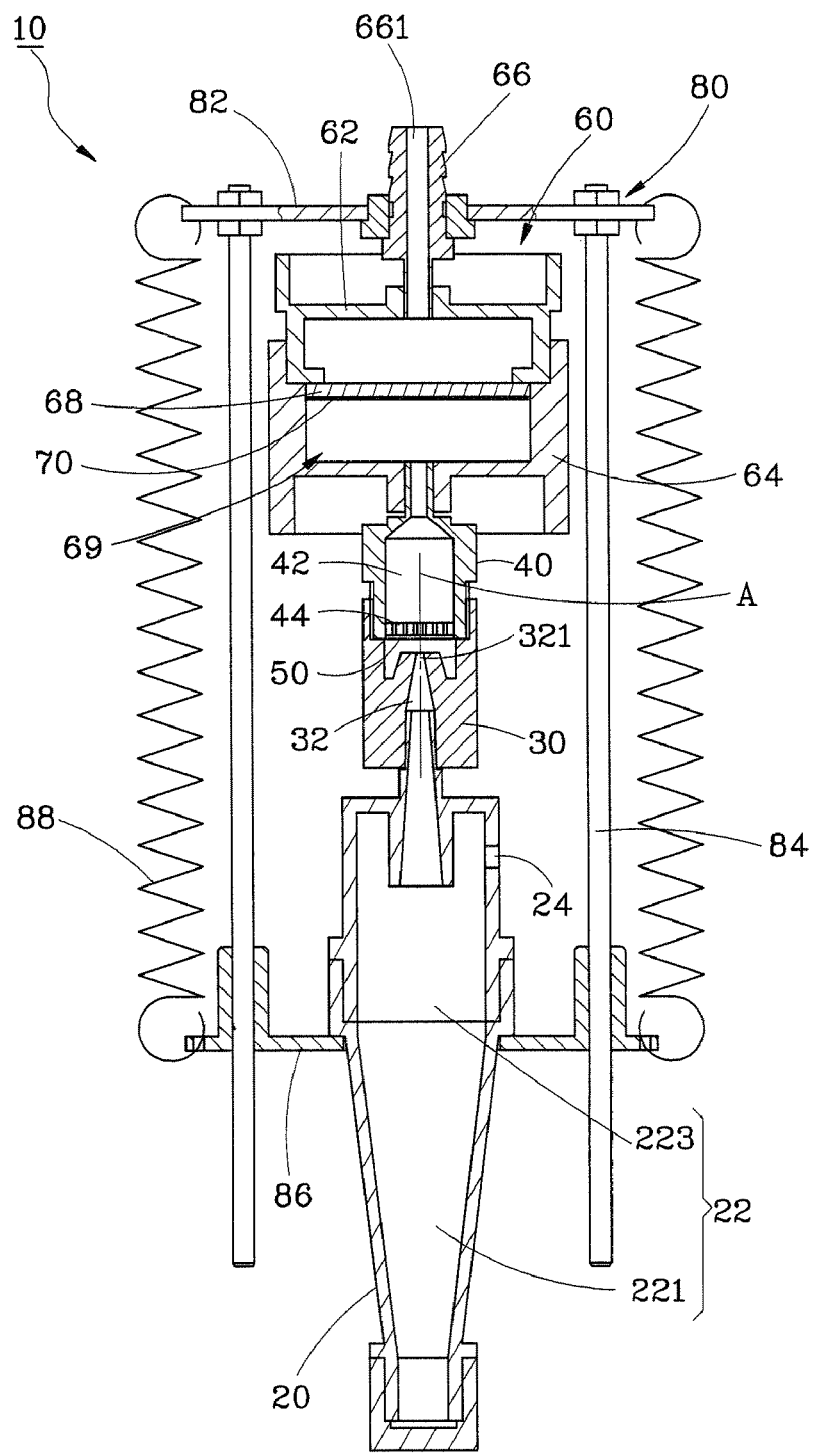
FIG. 3 is a sectional view of the personal nanoparticle sampler in accordance with the present invention.
Figure 4:
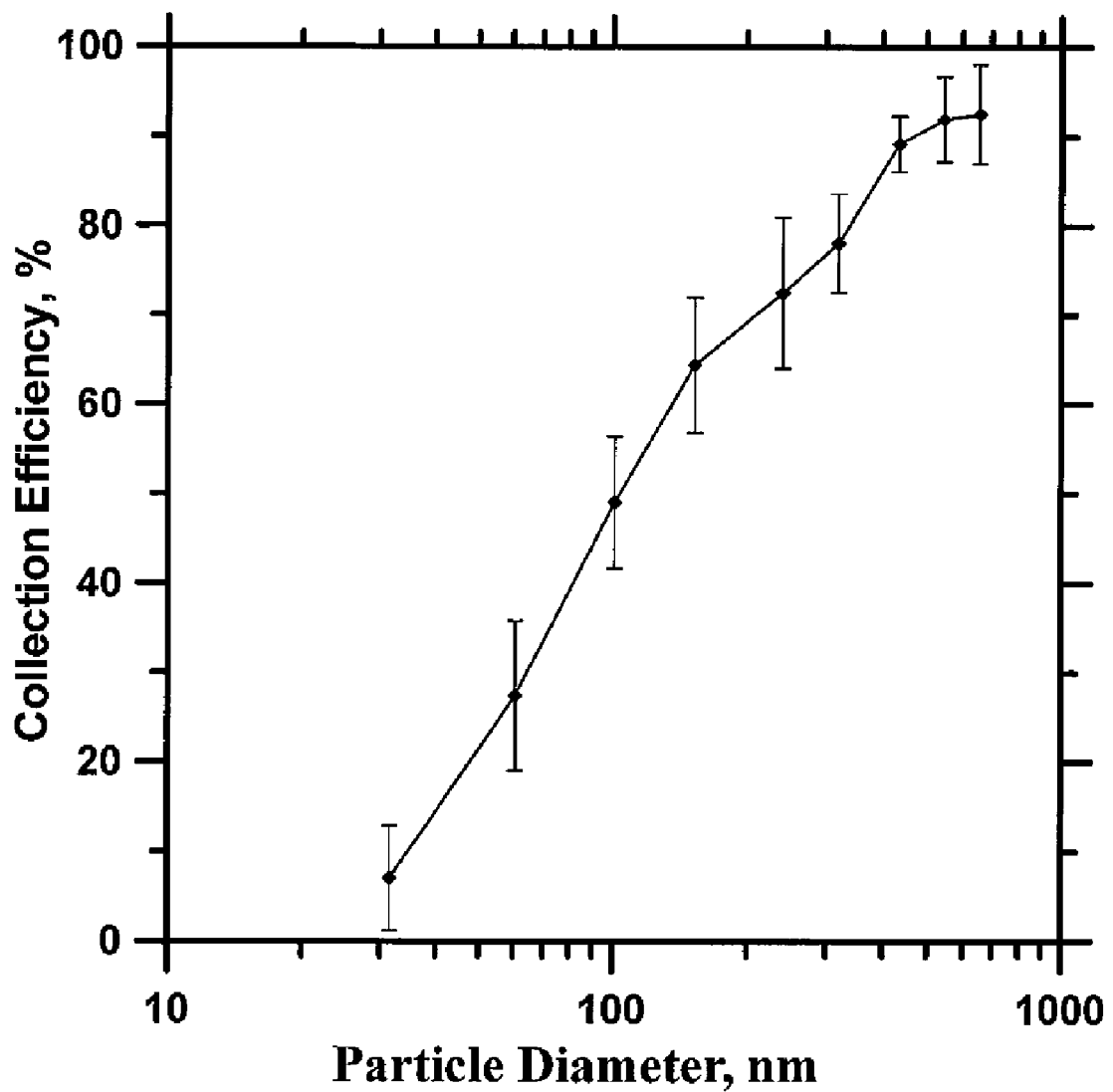
FIG. 4 is a particle collection efficiency curve of the personal nanoparticle sampler according to the present invention.

Referring to FIGS. 1~3, a personal nanoparticle sampler 10 in accordance with the present invention is shown comprised of a pre-classifier 20, a nozzle 30, a connector 40, a particle-sizing filter 50, a final filter pack 60, a final filter 70, and a rack 80.

The pre-classifier 20 is a cyclone separator, having a first chamber 22 and an air inlet 24. The first chamber 22 comprises a conical portion 221 and a cylindrical portion 223. The air inlet 24 extends from the cylindrical portion 223 of the first chamber 22 to the outside of the pre-classifier 20. According to the present preferred embodiment, the cylindrical portion 223 has an inner diameter of 17 mm. When the flowrate is at 5.3 L/min, the cut-off aerodynamic diameter of the cyclone separator 20 is about 3 μm.

The nozzle 30 is connected to the pre-classifier 20, having a passage 32 connected to the first chamber 22 of the pre-classifier 20. The cross section of the passage 32 reduces gradually in direction apart from the first chamber 22. The nozzle 30 comprises an air outlet 321 located on one end of the passage 32 remote from the first chamber 22 of the pre-classifier 20. The diameter of the air outlet 321 is also called the nozzle diameter. According to the present preferred embodiment, the cross section of the passage 32 has a circular shape and the air outlet 321 has a diameter of 1 mm.

The connector 40 is connected to one end of the nozzle 30 opposite to the pre-classifier 20, comprising a second chamber 42 and a filter support 44. The second chamber 42 is disposed in communication with the passage 32 of the nozzle 30. The filter support 44 is mounted in the second chamber 42, having a plurality of perforations 441.

The particle-sizing filter 50 is a PCTE (polycarbonate track etch) membrane arranged on the upstream side of the filter support 44 of the connector 40 within the second chamber 42. The particle-sizing filter 50 can be selected from, but not limited to, a PCTE (polycarbonate track etch) membrane of pore size 8 μm, 10 μm or 20 μm. Further, two or more particle-sizing filters 50 may be stacked up to reduce the cut-off aerodynamic diameter.

The final filter pack 60 comprises a top cover 62, a bottom cover 64, a connector 66, and a supporting pad 68. The top cover 62 and the bottom cover 64 are fastened together, defining a third chamber 69. The third chamber 69 is disposed in communication with the second chamber 42 of the particle-sizing filter pack 40. The connector 66 is installed on the top cover 62, defining therein a suction passage 661. The suction passage 661 extends from the third chamber 69 to the outside of the final filter pack 60. The connector 66 is connected to a suction pump (not shown) so that the inner of the first chamber 22, the passage 32, the second chamber 42 and the third chamber 69 of the personal nanoparticle sampler 10 are kept in a negative pressure condition for enabling surrounding particles to be sucked into the inside of the personal nanoparticle sampler 10 through the air inlet 24 of the pre-classifier 20. The supporting pad 68 is accommodated in the third chamber 69.

The final filter 70 is accommodated in the third chamber 69 of the final filter pack 60 and arranged on the upstream side of the supporting pad 68. The final filter 70 can be selected from, but not limited to, Teflon filter, quartz filter or MCE (mixed cellulose ester) membrane.

The rack 80 comprises a top plate 82, two sliding rods 84, a bottom plate 86, and two springs 88. The top plate 82 is stopped outside the final filter pack 60. The sliding rods 84 have the respective top ends respectively fastened to the top plate 82. The bottom plate 86 is coupled to the periphery of the pre-classifier 20 and movable along the sliding rods 84. The two springs 88 are bilaterally connected between the top plate 82 and the bottom plate 86. Under the effect of the spring force of the springs 88, the pre-classifier 20, the nozzle 30, the connector 40 and the final filter pack 60 are held together.

During the operation of the personal nanoparticle sampler 10, surrounding particles are moved with the intake flow of air into the first chamber 22, and the intake flow of air is caused to spin helically therein. At this time, relatively greater particles are caused by the centrifugal force to move toward the inside wall of the pre-classifier 20 and deposit on the bottom side of the first chamber 22, and therefore relatively greater particles are separated from the air flow.

When relatively greater particles are separated from the airflow spinning in the first chamber 22, relatively smaller particles are moved with the spinning air flow through the passage 32 and the air outlet 321 to the upstream side of the particle-sizing filter 50. Theoretically, when the filtration velocity of the particle-sizing filter 50 exceeds 72 m/sec, the cut-off diameter of the particle-sizing filter 50 will be reduced to below 200 nm. Because the air outlet 321 of the nozzle 30 is small, the filtration velocity of the particle-sizing filter 50 can be raised without increasing the total flowrate, thereby lowering the cut-off diameter of the particle-sizing filter 50. The diameter of the air outlet 321 is suggested to be smaller than 1.5 mm, preferably within 0.6 mm~1 mm. The particles which flow into the nozzle 30 move along an axis A of the passage 32 of the nozzle 30 until passing through the particle-sizing filter 50 and the perforations 441 of the filter support 44.

Thereafter, nanoparticles greater than a certain size (or called cut-size) are removed from the airflow, and smaller nanoparticles are moved with the airflow through the particle-sizing filter 50 into the third chamber 69 of the final filter pack 60 and collected by the final filter 70. After sampling, the exposure of workers to nanoparticles is determined by analyzing the composition and weight of the nanoparticles at the particle-sizing filter 50 and the final filter 70.

FIG. 4 is a particle size-collection efficiency curve obtained experimentally. In this experiment, the range of the particle diameter is from 31.6 nm~656.6 nm. The air flowrate of the personal nanoparticle sampler 10 is 5.3 L/min (i.e., the velocity of the air flow at the outlet 321 of the nozzle 30 is about 112.5 m/sec.), the diameter of the nozzle is 1 mm and the particle-sizing filter 50 has a pore diameter of 20 μm.

The inventor utilized a collision atomizer TSI model 3076 to generate polydisperse sodium chloride particles, and then utilized a diffusion dryer and an impactor to remove water vapor and large particles from the air respectively, and then utilized a DMA (differential mobility analyzer) to select monodisperse particles of a particular size, and then delivered the particles of a particular size into the personal nanoparticle sampler 10, and then utilized a CPC (condensation particle counter) TSI model 3022 to measure the number concentration of the particles passing through the particle-sizing filter 50. The number concentration of the particles passing through the particle-sizing filter 50 was compared with the number concentration of the particles before passing through the particle-sizing filter 50 to determine the particle collection efficiency.

As indicated in the experiment result, under the aforesaid experiment parameters, the cut-off diameter of the particle-sizing filter 50 of the personal nanoparticle sampler 10 is about 104 nm, i.e., particles greater than 104 nm can be removed by the particle-sizing filter 50, and particles smaller than 104 nm can pass through the particle-sizing filter 50.

The personal nanoparticle sampler 10 utilizes the nozzle 30 to accelerate filtration velocity, thereby lowering the cut-off diameter of the particle-sizing filter 50, and therefore the personal nanoparticle sampler 10 can sample nanoparticles at a low flowrate. Additionally, the pressure drop of the personal nanoparticle sampler 10 is relatively lower than conventional nanoparticle samplers. Therefore, the personal nanoparticle sampler 10 can be used with a portable personal suction pump and carried by a worker to sample surrounding particles at the workplaces.

Further, the designer can change of the pore diameter of the particle-sizing filter 50 or modify the diameter of the air outlet 321 of the nozzle 30, the distance between the outlet 321 of the nozzle 30 and the particle-sizing filter 50, and/or the flowrate of the suction pump, thereby changing the cut-off diameter of the particle-sizing filter 50. Further, the flow velocity at the outlet 321 of the nozzle 30 can be within 85 m/sec~165 m/sec, preferably within 110 m/sec~115 m/sec.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A personal nanoparticle sampler comprising:

a pre-classifier having a first chamber and an air inlet extending from the said first chamber to the outside of the said pre-classifier;

a nozzle connected to said pre-classifier, the said nozzle having a passage disposed in connection with the said first chamber of the said pre-classifier, the said passage having a cross section gradually reducing in the direction apart from said first chamber;

a connector connected to one end of the said nozzle opposite to the said pre-classifier, the said connector having a second chamber disposed in connection with the said passage of the said nozzle;

a final filter pack connected to the said connector, the said final filter pack having a third chamber and a suction passage, the said third chamber disposed in connection with the said second chamber of the said connector, the said suction passage extending from the said third chamber to the outside of the said final filter pack; and a rack having a top plate, two sliding rods, a bottom plate, and two springs, the said top plate being stopped outside the said final filter pack, the said sliding rods being connected to the said top plate, the said bottom plate being coupled to the periphery of the said pre-classifier and movable along the said sliding rods, the said springs being bilaterally connected between the said top plate and the said bottom plate.

2. The personal nanoparticle sampler as claimed in claim 1, wherein the connector further comprises a filter support mounted in the second chamber, the filter support having a plurality of perforations, particles which flow into the nozzle moving along an axis of the passage of the nozzle until passing through the perforations of the filter support.

3. The personal nanoparticle sampler as claimed in claim 1, wherein the said pre-classifier is a cyclone separator, and the said first chamber is comprised of a conical portion and a cylindrical portion.

4. The personal nanoparticle sampler as claimed in claim 1, wherein the said final filter pack comprises a top cover, a bottom cover, and a connector, the said top cover and the said bottom cover defining therein the said third chamber, the said connector defining therein the said suction passage.

5. The personal nanoparticle sampler as claimed in claim 1, further comprising a particle-sizing filter mounted in the said second chamber of the said connector.

6. The personal nanoparticle sampler as claimed in claim 5, wherein the said particle-sizing filter is a polycarbonate track etch membrane.

7. The personal nanoparticle sampler as claimed in claim 1, further comprising a final filter mounted in the said third chamber of the said final filter pack.

8. The personal nanoparticle sampler as claimed in claim 1, wherein the said passage of the said nozzle has a circular cross section and an outlet disposed at one end thereof remote from the said first chamber, the said outlet having a diameter smaller than 1.5 mm.

9. The personal nanoparticle sampler as claimed in claim 8, wherein the diameter of the said outlet is within 0.6 mm~1 mm.

10. The personal nanoparticle sampler as claimed in claim 1, wherein the said passage of the said nozzle has an outlet disposed at one end thereof remote from the said first chamber, the said outlet having an airflow velocity of 85 m/sec~165 m/sec.

11. The personal nanoparticle sampler as claimed in claim 10, wherein the airflow velocity of the said outlet is within 110 m/sec~115 m/sec.

\* \* \* \* \*